(12) United States Patent
Larenas

(10) Patent No.: US 7,168,114 B1
(45) Date of Patent: Jan. 30, 2007

(54) MEDICAL DEVICE ARM REST

(76) Inventor: William Larenas, 15 Cameo La., Westbury, NY (US) 11590

(*) Notice: Subject to any disclaimer, the term of this patent is extended or adjusted under 35 U.S.C. 154(b) by 0 days.

(21) Appl. No.: 11/209,337

(22) Filed: Aug. 23, 2005

(51) Int. Cl.
*A47G 9/10* (2006.01)

(52) U.S. Cl. ............................. 5/646; 5/632; D6/601

(58) Field of Classification Search .............. 5/646, 5/647, 632, 636; D6/601
See application file for complete search history.

(56) References Cited

U.S. PATENT DOCUMENTS

| | | | | |
|---|---|---|---|---|
| 1,787,832 A * | 1/1931 | Mueller | | 5/636 |
| D94,702 S * | 2/1935 | Marks | | D6/601 |
| 2,149,140 A * | 2/1939 | Gonzalez-Rincones | | 5/632 |
| 2,577,595 A * | 12/1951 | Tobias | | 5/632 |
| 2,782,427 A * | 2/1957 | Ericson | | 5/632 |
| 4,173,048 A * | 11/1979 | Varaney | | 5/632 |
| 4,210,317 A * | 7/1980 | Spann et al. | | 5/647 |
| 4,235,472 A * | 11/1980 | Sparks et al. | | 297/392 |
| D258,793 S * | 4/1981 | Rinz | | D6/601 |
| 4,270,235 A * | 6/1981 | Gutmann | | 5/646 |
| 4,574,412 A * | 3/1986 | Smith | | 5/632 |
| 4,730,801 A * | 3/1988 | Cloward | | 248/118 |
| 4,731,890 A * | 3/1988 | Roberts | | 5/655 |
| 4,901,384 A * | 2/1990 | Eary | | 5/632 |
| 5,097,551 A * | 3/1992 | Smith | | 5/652 |
| 5,109,557 A * | 5/1992 | Koy et al. | | 5/655 |
| D382,163 S * | 8/1997 | Hartney | | D6/597 |
| 5,815,863 A * | 10/1998 | Dolisi | | 5/632 |
| D409,038 S * | 5/1999 | Rojas et al. | | D6/601 |
| D416,743 S * | 11/1999 | Shelton | | D6/601 |
| D419,819 S * | 2/2000 | Bartoli | | D6/601 |
| D431,745 S * | 10/2000 | Jackson | | D6/601 |
| 6,622,727 B2 * | 9/2003 | Perry | | 128/845 |
| 6,691,353 B2 * | 2/2004 | Fuhriman | | 5/646 |
| D493,324 S * | 7/2004 | Rodgers | | D6/601 |
| 2003/0014820 A1 * | 1/2003 | Fuhriman | | 5/646 |

* cited by examiner

*Primary Examiner*—Robert G. Santos
(74) *Attorney, Agent, or Firm*—Thomas A. O'Rourke; Bodner & O'Rourke, LLP

(57) ABSTRACT

An arm positioning device for scanning devices and the like is described. The device has a top surface, a bottom surface, a first leg and a second leg. Each of the legs has a first end and a second end. The first end of each leg has a height less than the height of the second end of each leg. The second ends of the legs are connected to a body portion. The body portion has a height greater than the first ends of the legs.

12 Claims, 4 Drawing Sheets

MEDICAL DEVICE ARM REST

FIELD OF THE INVENTION

The present invention is directed to improvements in apparatus for taking scans such as CAT scans and the like. More particularly, the invention relates to devices that aid in positioning a patient where a CAT scan or other scanning device is used and more specifically for positioning a patient during scans as part of a breast examination for possible breast cancer.

BACKGROUND OF THE INVENTION

Breast cancer is a type of cancer in which cells in the breast become abnormal and grow and divide uncontrollably. Normal cells divide, grow, and die on a continual, controlled basis. The nucleus of each cell contains genes made up of DNA that determines its lifespan. When cells grow uncontrollably, they will eventually form a mass, also called a tumor. Benign tumors are not cancer, they do not invade other types of tissue, but they may pose problems depending on their size and location if they grow large enough to interfere with a bodily function (such as blood or urine flow) or put too much pressure on an organ or nerve. Malignant tumors are made up of abnormal cells that are capable of invading nearby tissues. Cells from the original tumor may also break off and travel via the blood or lymph systems to distant location (metastasize).

Most breast cancers are slow-growing and by the time a lump can be felt, it may have been growing for 5 or 10 years. Early breast cancer usually has no symptoms and the earlier a tumor is found, the better the chance of survival. For these reasons it is extremely important for women to be screened regularly by mammography or ultrasound since they may identify a cancerous tumor before it can be felt. In addition, if a lump or thickening can be felt, it is vital to seek a medical evaluation right away.

There are different types of breast cancer. One type of breast cancer is ductal cancer. The duct cells form the tissue that drains breast milk to the nipple. There are many groups of ducts and they all drain together at the nipple. The cells that make up the ducts can become cancer cells. When cancer cells develop in the duct tissue the cancer is called "ductal carcinoma in situ. Ductal cancer cells can grow through the ducts and into nearby tissues. When breast cancer cells grow beyond the ducts, it is called invasive ductal carcinoma. The cancer cells started in the duct tissue and grew into other tissues such as lymph or blood vessels or into the supporting (or stromal) tissue around the ducts. Invasive ductal cancers are measured by tumor size, which is important when planning each patient's treatment. Invasive ductal cancer means the cancer cells have invaded the tissue next to the milk ducts. It also means the cells can spread from the original tumor to nearby lymph nodes and/or to other organs (lungs, liver, bones).

A second type of breast cancer is called lobular carcinoma. The lobular tissue is the milk-producing gland tissue of the breast. It is arranged in clusters or rings of cells. Each cluster is called a gland. The glands produce the breast milk that goes into the ducts. Cancer that starts in the lobular tissue is different from ductal cancer. Lobular carcinoma in situ (LCIS) is an area of precancerous cells that are unlikely to become invasive cancer. But these abnormal cells in a lobule show that the woman has a high risk of developing invasive breast cancer. Lobular breast cancer is more likely to develop in both breasts than is ductal cancer.

There are some other types of breast cancer that affect women and do not fit into the ductal or lobular categories. These are described briefly below:

1) Inflammatory Breast Cancer—this type of breast cancer starts as a rash in the skin of the breast. It is uncommon and aggressive.

2) Sarcoma or Paget's disease of the breast-another rare form of breast cancer that does not begin with abnormal cells of breast tissue. It starts in the support tissues of the breast.

3) Lymphoid breast cancer—this is a form of lymphoma, a cancer of the lymph tissues.

There are different ways of screening the body for anomalies including cancerous tissues. For example, when an x-ray picture is taken through an object, the three-dimensional interior appears only as a two-dimensional picture, the details from front to back of the object appear superimposed and the picture is difficult to interpret. One method of carrying out an examination of a body by X-radiation is known as tomography. In tomography, a source of radiation is orbited relative to the body being examined, about an axis in or near the body, while a plate or other screen sensitive to the radiation transmitted through the body is displaced in such a way that the elements in one plane of the body remain substantially stationary. One type of tomography is a computerized axial tomography scan (CAT scan). In a cat scan, a series of detailed pictures of areas inside the body, taken from different angles; the pictures are created by a computer linked to an x-ray machine. This approach is also called computed tomography (CT scan) or computerized tomography. A CT Scan or CAT Scan has the ability to image soft tissue, bone, and blood vessels. Unlike other medical imaging techniques, such as conventional x-ray imaging (radiography), CT enables direct imaging and differentiation of soft tissue structures, such as liver, lung tissue, and fat. CT is especially useful in searching for large space occupying lesions, tumors and metastasis and cannot only reveal their presence, but also the size, spatial location and extent of a tumor. The CT scanner is a doughnut-shaped machine that uses advanced x-ray technology to take pictures of cross-sections of your body, called 'slices.' CT can examine areas that cannot be seen on regular x-ray examinations. CT scanners use x-rays, but the amount of radiation is kept to an absolute minimum.

Another method that is used to scan a body maps the absorption coefficient of a two dimensional slice of a body from a knowledge of the line integral of the absorption coefficient along all lines intersecting the slice. The map is prepared by a process involving the application of, for example, Fourier inverting techniques.

In a still other method, a small radio active source moves so as to follow the motion of a detector at the other side of the body. A representation of the section similar to a roentgenogram is produced by causing a thin line of light to be generated across the face of an open-shutter CRT screen to represent the line of view of the detector. The line of light is moved across the screen face to correspond to the detector motion, and the film holder rotated step-wise to correspond with the angle of the detector. The brightness of the line of light is varied according to the counting rate from the detectors so that the film ultimately records a picture built up from a series of overlapping lines of varying brightness.

In another approach of examining at least part of the interior of a body uses penetration radiation such as X or γ rays. In this approach radiation from an external source is transmitted through the body in a plurality of rays traversing a plurality of respective paths at an initial angle or initial mean angle. The rays constitute a first set of rays in a single planar slice of said body. The cross-sectional dimensions of each ray are small in relation to the dimensions of the body. Radiation from the external source is transmitted through the body in further sets of rays similar to the first set of rays. These further sets are disposed in the planar slice at angles or mean angles different from each other and from the initial angle or initial mean angle. The sets of rays are such that every element of a two-dimensional matrix of elements of the body in the planar slice is intersected by a group of the rays. The group of rays are different for the different elements of the array. From each ray emerging from the body an output signal is derived representing the sum of the transmissions or absorption in the elements of the body intersected by the ray. Thus, sets of output signals corresponding to the sets of rays are derived sufficient to obtain the transmission or absorption of each element of the resulting matrix. From the output signals, by a process of successive approximations, there are derived resultant signals representing the transmission or absorptions of the elements of the matrix. The derivation of the resultant signals typically includes the steps of deriving a difference signal responsive to the difference between each output signal and its reconstruction from the last approximations to the resultant signals, and adjusting the approximations to the respective resultant signals in response to the difference signal. Finally, in response to the resultant signals a representation of the transmissions or absorptions of the elements of the slice of the body is produced.

One of the problems in using the scanning devices is that the area being scanned should not be blocked by other parts of the body. As a result, when a scan is being taken as part of a breast cancer diagnosis, the patient's arms cannot block the area being scanned. In addition, because of the sensitivity of the devices and the small areas being scanned, patient movement must be minimized. As a result, the patient must typically be placed in a reclining position with the patient's arms raised away from the side of the body.

Prior art scanning devices usually include an arm rest. One typical arm rest is of the type sold by Q-Fix. This is a mechanical device which can be adjusted to a variety of positions to accommodate different patient sizes and conditions. One of the problems encountered in using arm rests of these types is that they are difficult to adjust. Because they are designed to adjust to a variety of positions both horizontally and vertically, there are a great number of potential permutations that are possible and a great deal of time is taken to adjust the arm rest to each patient.

Besides the complexity of the prior art devices, these devices also suffer from significant cost. Another issue with these devices is tied into the issue of cost is disposability. These devices must be cleaned after each use by a patient. This is time consuming and adds labor cost to the scan.

As a result, there is a need for an improved arm rest for use with scanning machines and the like that does not have the drawbacks of the prior art.

OBJECTS OF THE INVENTION

It is an object of the present invention to provide an improved positioning device for increased patient comfort when scans are being taken.

It is also an object of the present invention to provide an improved arm rest for use with scanning devices so that a clear scan of the desired areas can be obtained.

It is another object of the invention to provide an article that it facilitates the ability of small, medium and large sized breast cancer patients to go through the CAT Scan bore freely.

It is another object of the invention to provide an improved positioning device that is easy to use for a variety of patients.

It is a further object of the invention to provide a positioning device that will place the patient in a more comfortable position.

It is a still further object of the invention to provide a positioning device that places the patient in a position for a scan where a great deal of individual adjustment is not required.

It is still another object of the invention to provide a positioning device that can be comfortably used with patients of different sizes and shapes.

It is another object of the invention to provide a device for positioning a patient's arm during a breast scan so that the arm does not interfere with the scan.

It is also an object of the invention to provide an arm rest for a breast scan examination that is easy to set up and use for different patients.

It is a further object of the invention to provide an arm rest for use with scanning machines that is of relatively low cost.

It is still another object of the invention to provide an arm rest for use with a scanning device that may be easily disinfected.

It is a still further object of the invention to provide an arm rest for a scanning device that is relatively low cost.

SUMMARY OF THE INVENTION

The present invention is directed to an improved positioning device for breast examinations and more particularly for scans such as CAT scans. The present invention permits the patient's arm to be readily positioned away from the scan area in a relatively comfortable position. The rest of the present invention can be used for either the right arm or the left arm. The present invention facilitates the ability of small, medium and large sized breast cancer patients to go through the CAT Scan bore freely.

The article of the present invention has generally an "L" shape with a base portion which is shaped to be positioned on the table where the patient reclines for the scan. In a preferred embodiment, the base surface is relatively flat. However, the shape of the base portion can be designed to fit any surface of the table where the patient is positioned. The article of the present invention has a first leg and a second leg. The first and second legs are typically disposed at above 90° to each other. The first leg, which is used for the humerus, is typically larger than the second leg. Each leg of the present invention has a first side wall and a second side wall opposite the first side wall. In one embodiment, the side walls may be joined by a base side wall at the end of each of the legs. The top surface of each of the legs is preferably angled, rising from each base side wall the body of the article. The body of the article is typically the section formed where the legs are joined and this is generally the area where the elbow rests during use.

The device may be made of any suitable material. One preferred material is a foamed material that is coated or covered with a fluid impermeable layer. In one embodiment, the covering is easily disinfected so that it can be reused. In this embodiment, the covering is preferably relatively smoothed surfaced so that it may be readily sanitized.

DETAILED DESCRIPTION OF THE DRAWINGS

Figure 1:
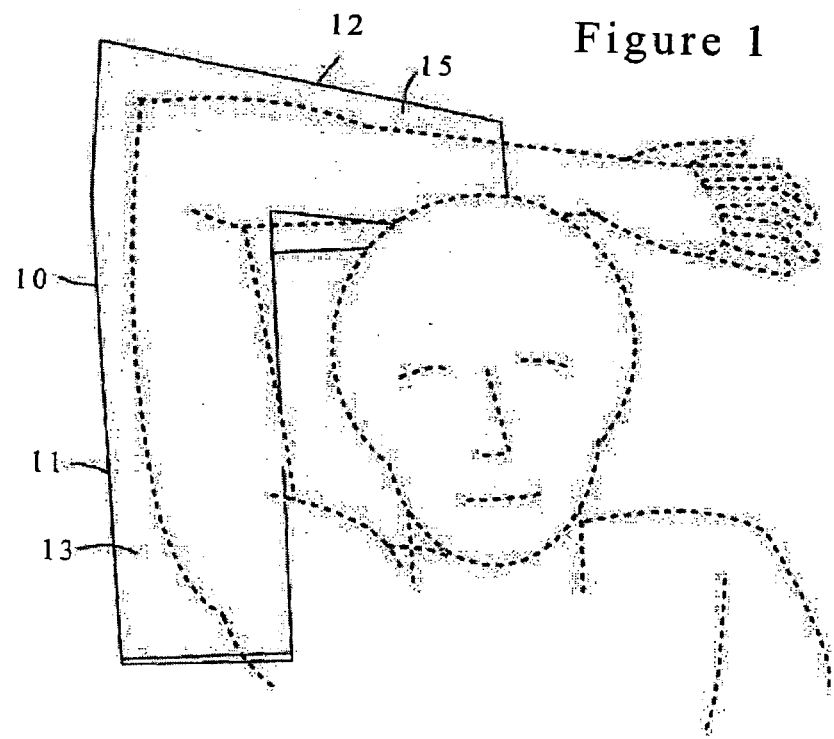
FIG. 1 is a top view of an example of the article of the present invention in use for the right arm with a representation of a patient on an examination or other type table (not shown).
Figure 6:
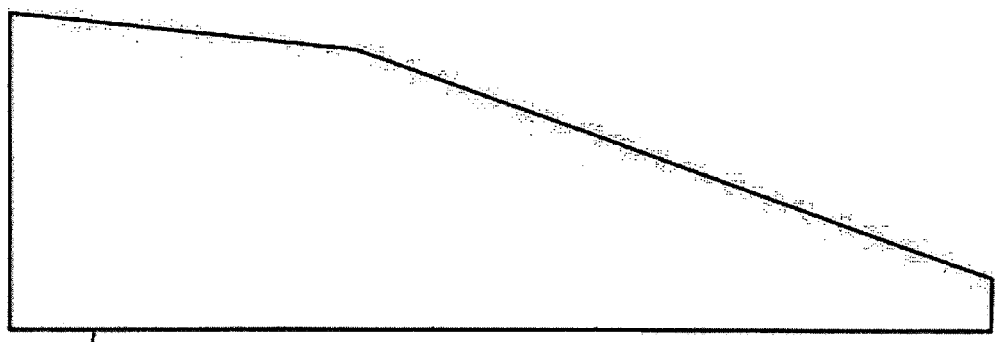
FIG. 6 is a side view of the article of FIG. 2 taken from direction D.
Figure 3:
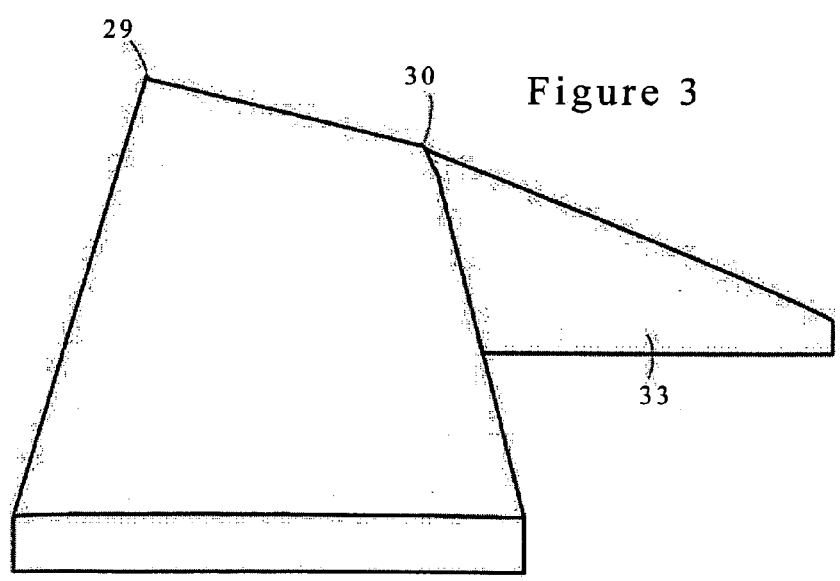
FIG. 3 is a side perspective view of the article of FIG. 2 taken from direction A.
Figure 4:
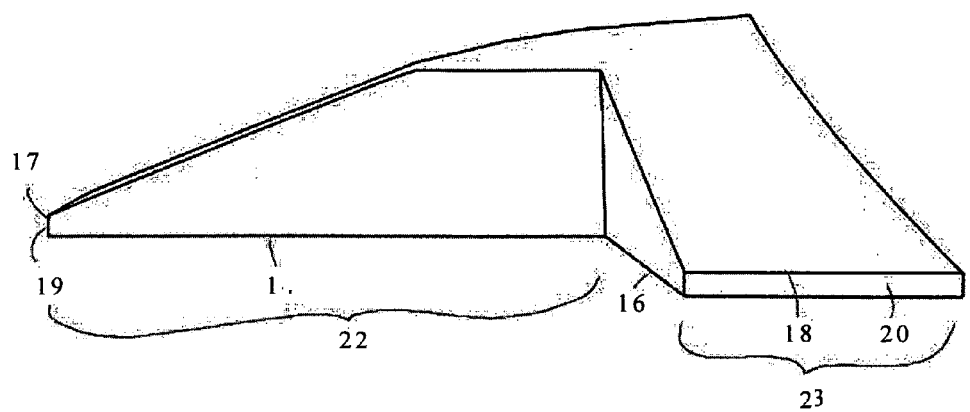
FIG. 4 is a side perspective view of the article of FIG. 2 taken from direction B.
Figure 7:
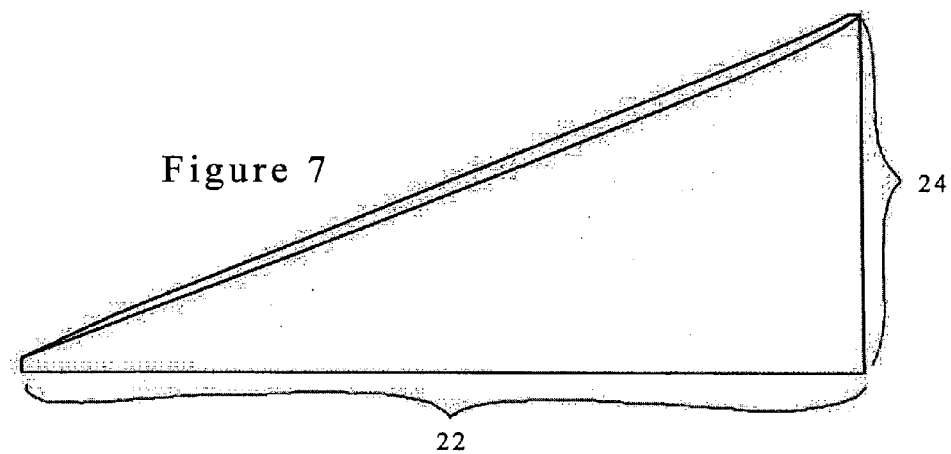
FIG. 7 is a side perspective view of the article of FIG. 2 taken from direction E.
Figure 5:
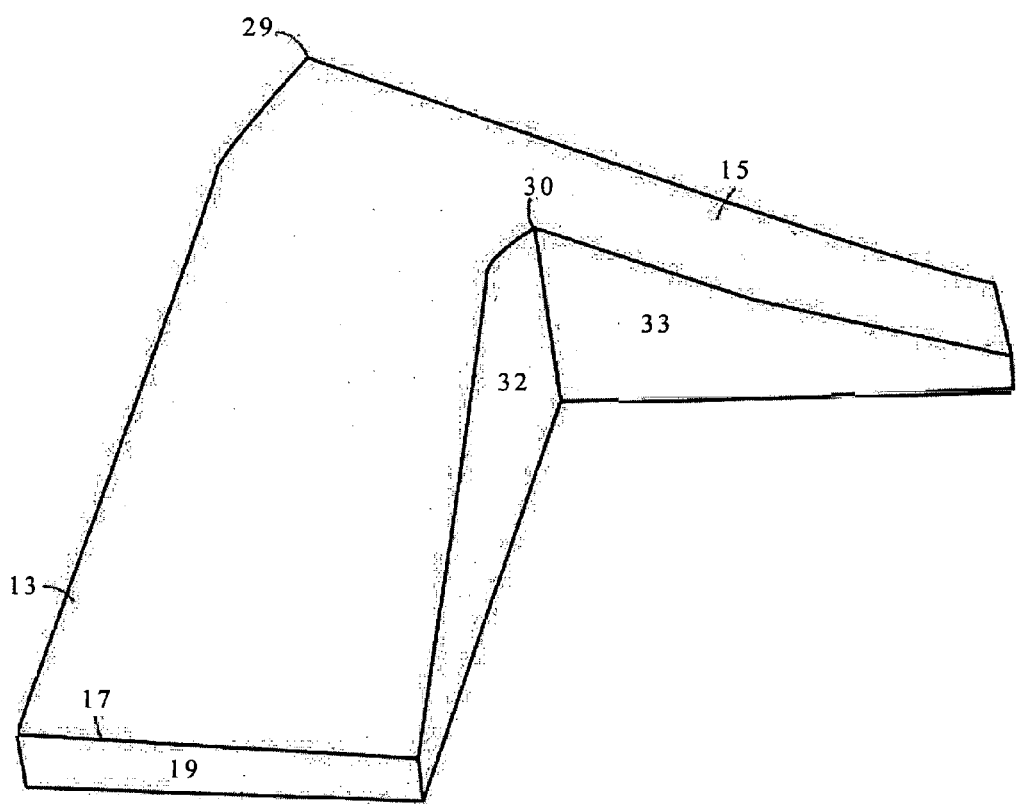
FIG. 5 is a side perspective view of the article of FIG. 2 taken from direction C.

As seen in FIG. 1, there is an arm positioning device 10 that permits the arm of a patient to rest while it is placed away from the patient's side so that a scan such as a CAT scan can be taken. The present invention has particular applicability for use with scans of a patient's breasts during examination for breast cancer. In fact, the present facilitates the ability of small, medium and large sized breast cancer patients to go through the CAT Scan bore freely. The arm positioning device permits the patient's arm to be in an at rest position so that the patient is relatively comfortable and less likely to move during the scan. Scans are very sensitive to movement and patient comfort will increase the likelihood of an accurate scan.

Figure 2:
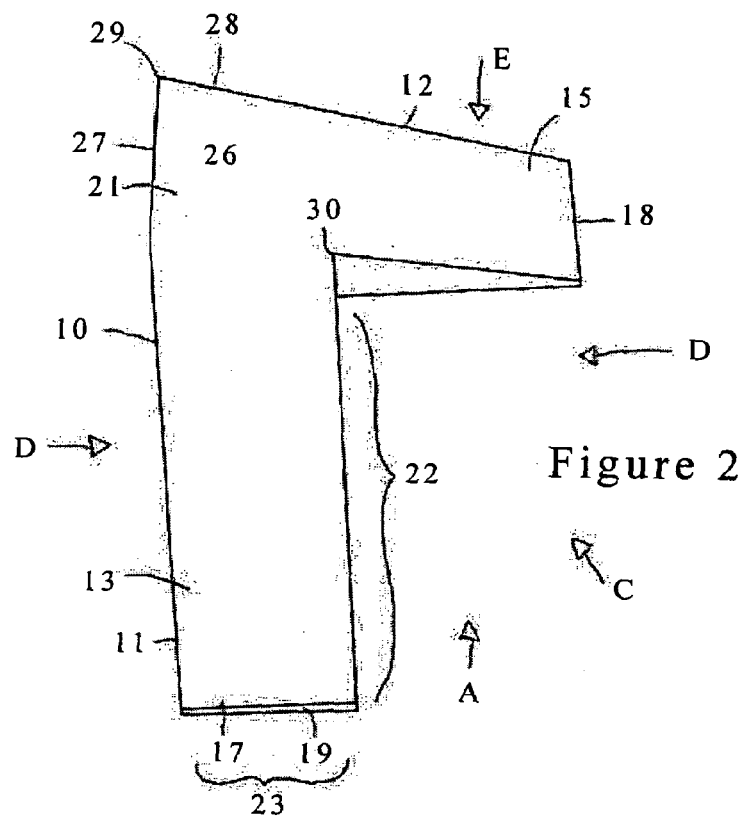
FIG. 2 is a top perspective view of the article of FIG. 1.

The positioning device 10 of the present invention is generally an "L" shaped arm rest having a first leg 11 and a second leg 12. The first leg 11 is preferably generally slightly longer than second leg 12. The first leg 11 is the portion of the positioning device for placing the patient's humerus. The second leg 12 is for supporting the patient's ulna. The article of the present invention shown in FIG. 1 is for the right arm. A mirror image of the rest shown in FIG. 2 can be used for the left arm. The arm rest raises the patient's arm away from the side of the chest so that an accurate scan may be taken. The article of the present invention places the forearm adjacent to the top of the patient's head so that it is also away from the side of the torso.

The first leg 11 has a top surface 13 and a bottom surface 14. Similarly, the second leg has a top surface 15 and a bottom surface 16. The bottom surface may be any configuration so that the bottom surface of the positioning device rests on the top surface of the scanner table (not shown) which supports the patient. Each of the top surfaces meet generally in the region where the elbow-joins the humerus with the ulna. The article of the present invention has a body 21 where the legs are joined.

The body 21 may have a bottom surface 25 that is generally in the same plane as the bottom surface of each of the legs. The body will also have a top surface 26 and a pair of side surfaces 27 and 28. The side surfaces 27 and 28 may be generally perpendicular to each other in a preferred embodiment. The top surface 26 of the body 21 may be a plane that is generally horizontal. Alternatively the top surface 26 of the body 21 may be in the same plane as the top surfaces 26 of either of the two legs 11 and 12. In a still further embodiment, the plane of the top surface of one leg can contact the top surface of the other leg above a line generally formed from the outer corner 29 formed by the intersection of the outer sidewalls of the body 21 and the inner corner 30 formed by the intersection of the inner sidewall 32 of the first leg and the inner sidewall 33 of the second leg.

The first leg has a length 22, a width 23 and a height 24. The second leg has a length 22', a width 23' and a height 24'. The height varies across the length of the legs with the highest point being generally at the body 21. The height 24 and 24' has its shortest dimension at the ends 17 and 18 of the legs 11 and 12. The height of the body portion can vary depending on the needs of the patient. For example, smaller patients including children may prefer a height of about 1" at the body 21, while older and/or larger patients may prefer to have the height for the body of 3"–4" or more, depending on the patient's comfort. As can be seen from the drawings, the free ends of the legs 17 and 18 are lower than the ends of the legs that are connected to each other to form the body 21. This permits the elbow region of the arm to be conveniently raised to a relatively comfortable position.

The free ends 17 and 18 can be formed by the intersection of the top surface 13 and the bottom surface 14 to form a point. The top surface 13 and the bottom surface 14 of the first leg form an angle less than 60°. One preferred angle is an acute angle. The size of the angle is preferably ≦45° and more preferably ≦35° and most preferably less than 30°. Similarly the free end 18 can be formed by the top surface 15 and the bottom surface 16. The top surface 15 and the bottom surface 16 can also form an angle less than 60°. One preferred angle is an angle ≦45° and more preferably less than 30°. The angle formed by top surface 13 and bottom surface 14 can be the same as or different from the angle formed by top surface 15 and bottom surface 16.

In another embodiment, the first leg 11 preferably has an end side wall 19. The distance of the side wall 17 from the bottom surface 14 to the top surface 13 can vary as desired for the patient's comfort. Similarly, the second leg 12 preferably has an end sidewall 20 as well.

Although the first leg and second legs have been shown generally at right angles to each other, it will be appreciated that the angle can be either greater than or less than that. In one preferred embodiment, the angle formed by the two legs can range from 60° to 120°. In another embodiment, the arm rest of the present invention may be more of a crescent shape with a curved inner surface and a curved outer surface. In this embodiment there are two ends, both of which have a low initial height or form a point when viewed from the side. Each leg rises from the end of the leg toward a center section which may form a plateau or high point for resting the elbow during the scan.

The device may be made of any suitable material. One preferred material is a foamed material that is coated or covered with a fluid impermeable layer. In one embodiment, the covering is easily disinfected so that it can be reused. In this embodiment, the covering is preferably relatively smoothed surfaced so that it may be readily sanitized. Suitable foams include but are not limited to polyurethane foam, ethylene vinyl acetate (EVA) foam, polyvinyl chloride (PVC) foam, ethylene polypropylene foam, polystyrene foam and polyisocyanate foam.

I claim:

1. An arm positioning device for medical imaging devices comprising a top surface, a flat bottom surface, a first leg and a second leg, said first and second legs disposed at an angle of about 90° or greater to each other said first leg being longer than said second leg, each of said first leg and said second leg, having a first sidewall and a second sidewall, each of said first leg and second leg having a first end and a second end, said first ends ending in a base sidewall said first end having a height less than the height of said second end, said second ends being connected to a body portion, said body portion having a height greater than said first ends said first and second sidewalls and said base sidewalls being generally at a right angle to said bottom surface.

2. The arm positioning device according to claim 1 wherein said first and second legs form a right angle to each other.

3. The arm positioning device according to claim 1 wherein said top surface and bottom surface of said first and second ends meet and form a point when said legs are viewed from a side of said device.

4. The arm positioning device according to claim 3 wherein the angle formed by said top surface and said bottom surface is 60° or less.

5. The arm positioning device according to claim 4 wherein the angle formed by said top surface and said bottom surface is 45° or less.

6. The arm positioning device according to claim 5 wherein the angle formed by said top surface and said bottom surface is 30° or less.

7. The arm positioning device according to claim 1 wherein said base sidewalls extend between said top and bottom surfaces and between said first sidewall and said second sidewall, said first and second sidewalls extending between said top surface and said bottom surface of said legs.

8. The arm positioning device according to claim 1 wherein said first leg of said device permits the humerus of a patient's arm to rest thereon and the second leg permits the patient's ulna to rest thereon.

9. The arm positioning device according to claim 8 wherein said patient's ulna is adjacent to the patient's head when the arm positioning device is used.

10. The arm positioning device according to claim 1 wherein the body portion has a first sidewall and a second sidewall generally perpendicular to each other, said first sidewall being in the same plane as a sidewall formed on said first leg between said top surface and said bottom surface and wherein said second sidewall being in the same plane as a sidewall formed on said second leg between said top surface and said bottom surface.

11. The arm positioning device according to claim 10 wherein a third sidewall on said first leg formed between said top surface and said bottom surface intersects with a fourth sidewall formed between said top surface and said bottom surface of said second leg.

12. An arm positioning device for medical imaging devices comprising:

a top surface; and a flat bottom surface; and a first leg and a second leg, said first and second legs disposed at an angle of about 90° or greater to each other, said first leg being longer than said second leg, each of said first leg and said second leg, having a first sidewall and a second sidewall, each of said first leg and second leg having a first end and a second end, said first ends ending in a base sidewall said first end having a height less than the height of said second end, said second ends being connected to a body portion, said body portion having a height greater than said first ends, said body portion having at least a portion of its top surface having a height greater than the height of said legs, said first and second sidewalls and said base sidewalls being generally at a right angle to said bottom surface, said top surface of said body portion being in generally the same plane of the top surface of one of said legs.

* * * * *